United States Patent [19]

Forusz et al.

[11] 3,977,202

[45] Aug. 31, 1976

[54] COLD PACK DEVICE

[75] Inventors: Samuel Laurence Forusz, Trenton; William Frank Vinczi, Edison; Milton Ralph Cross, Freehold, all of N.J.

[73] Assignee: Johnson & Johnson, New Brunswick, N.J.

[22] Filed: May 28, 1975

[21] Appl. No.: 581,452

[52] U.S. Cl. .............................. 62/4; 252/188.3 R; 206/219; 128/403
[51] Int. Cl.² ........................................... F25D 5/00
[58] Field of Search .............. 62/4, 457, 94; 44/3 R, 44/3 A; 252/70, 188.3 R, 194; 206/219, 222; 128/403

[56] References Cited
UNITED STATES PATENTS

| 1,894,775 | 1/1933 | Levenson | 62/4 |
|---|---|---|---|
| 2,185,799 | 1/1940 | Blake et al. | 62/4 |
| 2,916,886 | 12/1959 | Robbins | 62/4 |
| 3,058,313 | 10/1962 | Robbins | 62/4 |
| 3,191,392 | 6/1965 | Donnelly | 62/4 |
| 3,893,834 | 7/1975 | Armstrong | 62/4 |

FOREIGN PATENTS OR APPLICATIONS

| 338,537 | 11/1930 | United Kingdom | 62/94 |
|---|---|---|---|

*Primary Examiner*—Stephen J. Emery
*Attorney, Agent, or Firm*—Steven P. Berman

[57] ABSTRACT

A cold pack device comprising an anhydrous salt, salt hydrate and a water miscible organic liquid, wherein said components are contained in a package such that they are separated until activation is desired and upon activation the components are mixed and an endothermic reaction occurs resulting in a lowering of the temperature of the mixture to a therapeutic range and maintaining said temperature for a substantial time duration.

8 Claims, No Drawings

COLD PACK DEVICE

BACKGROUND OF THE INVENTION

This invention relates to cold pack devices. More specifically, this invention relates to cold pack devices which can be utilized for treating injury and reducing pain.

The treatment of injury by the application of cold pack devices is known as cryotherapy or cold treatment. For many years, physicians, trainers and coaches of athletic teams have utilized the application of cold to treat sprains or fractures. It is also well known that cold is an effective medical treatment for other medical problems as well. Cold is also used to slow bleeding, for example, nosebleeds and the like, to reduce the pain and swelling of wounds, to slow the absorption of snake bite poisons by reducing the blood flow in the bite area and for other medical applications.

When an injury occurs, the blood vessels in the area dilate and release fluid into the injured tissue, thus causing swelling and pain. This swelling is due to damage of the capillary wall which results in seepage of fluid to the injury site. Reducing the circulation in the area by application of cold reduces the accumulation of fluid and thereby minimizes the swelling in the area. In the management of injuries the prevention of swelling is desirable. The early application of a cold pack device to the injured area constricts the blood vessels and reduces the loss of fluid into the injured area. Thus, while cold therapy reduces the circulation to the site of injury, it is only for a relatively short period of time. It prevents the swelling which would prolong the period of disability and thus retard healing.

Cold also relieves the pain of an injury by desensitizing nerve endings. When cold is first applied to an affected area, there is a gradual onset of numbness produced by a slowing of the sensory conduction. Then there is an inhibition of all sensory perception of the area, including pain. The application of cold to an injured surface also helps to stop bleeding. For example, cold is effective in reducing the disabling effects of bruises and sprains. It slows the leakage of blood by reducing the blood flow to the area and therefore from ruptured capillaries. The black-and-blue discoloration of the skin is due to a leakage of blood from ruptured blood vessels. By applying a source of cold to the injured area, the temperature of the skin drops and the blood vessels constrict. This helps to promote the clotting of the ruptured capillaries, thereby reducing local blood loss and swelling.

In the early treatment of first or second degree burns, the application of cold will again slow the blood flow and thereby reduce the massive swelling which usually accompanies burns.

Thus, it is well known that the prompt and efficient medical application of cold has desirable medical advantages. The old and long-accepted medical method of supplying needed cold was to fill a rubber bag with ice, wrap the icebag with a towel, and apply it to the area of injury. This method, although effective, often takes considerable time and is obviously impossible at the scene of an accident, on an athletic field, or in a first-aid station or hospital emergency department.

To eliminate inconvenience and to facilitate the use of cold, various disposable cold pack devices that require no refrigeration have been developed and made commercially available. These devices generally consist of chemicals in a plastic bag containing two or more compartments in order to keep the chemicals separated until actuation is desired. The "instant ice pack," as these devices are sometimes referred to, are initiated by rupturing or removing the separating means to produce an endothermic reaction, that is, as a result of the chemical reaction, cold is produced by the absorption of heat from the surroundings. These devices in many cases have various negatives which reduce their effectiveness and, therefore, their desirability. For example, some of these cold pack devices contain materials which do not have negative heats of reaction sufficient to result in a final temperature within the optimum therapeutic range, i.e., 30°–45°F. Temperatures below 30°F. may be desirable for certain applications. Other cold pack devices have undesirable slow activation times while still others present cost problems or problems at shipping or storage temperatures. One of the most significant shortcomings of the prior products has been the inability of such cold pack devices to produce or maintain the desired effective temperature over a sustained period of time. Still another significant shortcoming of the presently available cold packs is that such products when activated at higher ambient temperatures, i.e., 90° to 100°F., do not drop to the desired therapeutic temperature range.

Typical attempts of the prior art to form a desirable cold pack device include U.S. Pat. Nos. 2,898,744 and 3,058,313. U.S. Pat. No. 2,898,744 discloses chemical freezing packages which consist of chemicals such as sodium acetate, ammonium chloride, sodium nitrate, sodium thiosulfate, potassium iodide, calcium chloride, and ammonium nitrate which upon the addition of water result in a marked reduction of temperature.

U.S. Pat. No. 3,058,313 discloses a cooling pack comprising a crystalline form of a chemical reagent in admixture or contact with a dry form of a chemical. The dry form of chemical is said to be ammonium nitrate ($NH_4NO_3$) and the crystalline reagent is said to be sodium carbonate decahydrate ($Na_2CO_3 \cdot 10H_2O$) or a similar chemical reagent. It is further indicated that the water of crystallization is sufficient to cause the necessary freezing reaction although additional water may be added if desired.

Cold pack devices prepared in accordance with the above and other similar teachings do not result in completely satisfactory products as previously discussed. For example, such products do not have the desired fast activation and long duration of cold and, furthermore, many of these formulations do not have a reusability feature.

For the purposes of this invention, the term "fast activation" is defined as the rapid drop in temperature of the cold pack device after it has been activated. The optimum standards set for fast activation for the purposes of this invention are that three minutes after activation the cold pack should fall to or below about 10°F. when activated at 40°F; to about 45°F. or below when activated at 70°F. or higher.

The term "duration of cold" as used in describing the present invention shall mean the length of time the activated cold pack remains at or below 45°F. The term "reusability" as used hereinafter shall mean that a cold pack device does not freeze solid but remains conformable and available for immediate use when placed in a freezer or other similar temperature regulating apparatus at 0°F. for 24 hours after the cold pack device has been activated and the endothermic reaction has ceased.

SUMMARY OF THE INVENTION

It is, therefore, a general object of the present invention to provide a cold pack device which overcomes the above-discussed negatives of such products that have previously been available to the consumer.

It is another object to provide a cold pack device which features fast activation and long duration of cold regardless of the initial activation temperature.

It is a further object of the present invention to provide a cold pack device which has reusability aspects.

It is a still further object to provide a cold pack device which when activated at elevated temperatures, e.g., 90° to 100°F, will reduce the temperature to the desired therapeutic range.

Other objects and advantages of the present invention will be readily apparent to one skilled in the art from the following description.

The foregoing objects and other features and advantages of the present invention are achieved by a cold pack device comprising a specific anhydrous salt, a specific salt hydrate and a specific water miscible organic liquid which, if desired, may be admixed with water to form an aqueous solution. When these components are mixed together after initially being separated by suitable packaging, an endothermic reaction occurs resulting in a rapid lowering of the temperature of the mixture. The mixtures of the present invention will not freeze solid when placed in a freezer compartment or atmosphere after the initial reaction has been completed and thus can be reutilized to provide an additional application of cold, as required.

DETAILED DESCRIPTION OF THE INVENTION

The cold pack devices of the present invention can be packaged utilizing any package which will allow the solid components, i.e., anhydrous salts and salt hydrates, and the liquid components, i.e., water miscible organic liquid and water, to be separated from each other prior to use and while in storage and yet be readily admixable when activated. While many packaging systems for accomplishing this result will occur to one skilled in the art, one such system comprises in its simplest form a sealed, rectangular envelope of a flexible, thin material such as, for example, polyethylene, said envelope being divided into two chambers by a separation means extending transversely across the envelope. The separation means should be one which will keep the chambers separated prior to use, but which can be removed as a barrier to flow between the chambers when the system is activated. Several such separation means are known in the art, one of which being described in U.S. Pat. No. 2,601,568, issued on June 24, 1952, to P. Sussenbach et al. and incorporated herein by reference. This patent describes an elongated clamping bar having a U-shaped cross-section and a core rod co-extensive with the clamping bar which is designed to be engaged within the U-shaped cross-section.

The clamping bar is disposed transversely on the exterior of one major surface of the envelope and the core rod is disposed on the exterior of the other major surface to provide the two chambers. The core rod is inserted into the U-shaped cross-sectional clamp bar, pinching the envelope material therebetween and dividing the envelope into two chambers sealed from each other. This seal may be easily broken during use by simply separating the clamping bar from the core rod. Generally, it is contemplated that each of the two so-formed chambers will contain one of the two solid components of the cooling system of this invention. The liquid components, i.e., the water miscible organic liquid and, if desired, water can be contained in a flexible liquid-impervious bag which may be disposed in either of the two chambers. This bag may have at least a portion of its wall weakened in some manner so as to fail and release the liquid upon application of pressure on the external surface of the envelope when the bag is disposed therein. Such weakening can also be accomplished by simply providing, for the walls of the bag, a material which is of thinner gauge than that of the outer envelope, so that a blow or pressure delivered on the external surface of the envelope will preferentially cause the inner bag to rupture. Alternatively, the bag may be provided with perforations cut partially into the walls which will completely rupture upon the application of pressure. Still another possibility is a combination of thin walls and perforations as can be accomplished by providing the bag with walls formed from a laminate of thin gauge material and a stronger material which has perforations therethrough.

In use, it is contemplated that the inner bag will first be broken by the application of pressure on the exterior of the envelope, thus allowing the liquid component to admix with the one solid component contained in that chamber of the envelope in which the bag is disposed. Thereafter, the seal between chambers is broken by removing the core rod from the clamping bar and accordingly, all the components can be admixed to produce the desired endothermic reaction taught herein resulting in the availability of the desired cold effect.

Other packaging systems which may be utilized for the cold pack compositions of the present invention include a package comprising a bag of a suitable material, e.g., polyethylene, divided into two or more compartments, said compartments separated by means of an internal adhesive, heat, or other rupturable seal. When activation of the cold pack device is desired, the rupturable seal is ruptured thereby permitting the components to come into contact with one another resulting in the desired endothermic reaction.

The anhydrous salts which are useful in the present invention include ammonium nitrate, potassium nitrate, ammonium chloride and the like. Ammonium nitrate is the preferred anhydrous salt from the point of view of effectiveness and cost.

The salt hyrates which are useful in the present invention include sodium acetate trihydrate, sodium carbonate decahydrate, sodium sulfate decahydrate, sodium thiosulfate pentahydrate, sodium phosphate dodecahydrate and the like. The preferred salt hydrate is sodium acetate trihydrate because of its ready availability and its high temperature stability which is a desired shipping and storage advantage.

The water miscible organic liquids which are useful in the present invention are the alkylene glycols containing from 2 to 4 carbon atoms such as ethylene glycol which is the preferred water miscible organic liquid.

The water miscible organic liquid can be utilized alone or in admixture with a suitable amount of water. It has surprisingly been found that the water miscible organic liquid either alone or admixed with water is a coreactant with the salt in the reaction with the salt hydrate to generate the desired cold. The water miscible organic liquid also provides a reusability feature to the cold pack device by preventing freezing when said device is placed in a freezer apparatus maintained at a temperature of freezing or below. It has further been found that by varying the proportions of the water miscible organic liquid and the water that activation of the cold pack device below 32°F. can be ensured.

A dye indicator can be added to the water miscible organic liquid or the aqueous solution thereof in order to serve as an indicator of the desired complete mixing of the components. If desired, a suitable flow agent or anti-caking agent can be added to the salt hydrate to prevent caking and to facilitate the easy and complete mixing of the components. Suitable flow or anti-caking agents include tricalcium phosphate, silica powders and the like.

The ratios of the anhydrous salt and salt hydrates and water miscible organic liquid utilized in the present invention can be varied with somewhat different results depending on the ratio. These ratios can be easily determined by simple experimentation for each desired system of salt and salt hydrate. For example, in the system comprising sodium acetate trihydrate and ammonium nitrate, it has been found that the best results are obtained when the two salt components are present in a ratio of about 1:1 with respect to each other. It has, however, been determined that effective cold pack devices can be prepared wherein the sodium acetate trihydrate and ammonium nitrate are each present in a range of from about 16 to 64% weight by weight of the total composition. It has also been found that at least 10% by weight of the total composition of the water miscible organic liquid is necessary in order to achieve the desired results of the present invention.

Specific embodiments of the present invention are illustrated by the following examples. It will be understood, however, that the invention is not confined to the specific limitations set forth in the individual examples, but rather to the scope of the appended claims.

EXAMPLES

The following compositions are prepared by admixing the components in closed containers equipped with a copper/constantin thermocouple temperature probe manufactured by Bailey Instruments Company, Inc. All weights are in grams.

| Ex. | $NH_4NO_3$ | $Na\ C_2H_3O_2.3H_2O$ | $H_2O$ | Ethylene Glycol |
| --- | --- | --- | --- | --- |
| 1 | 200 | — | 200 | — |
| 2 | 200 | 200 | — | — |
| 3 | 200 | 200 | 100 | — |
| 4 | 200 | 200 | — | 100 |
| 5 | 200 | 200 | 50 | 50 |

The closed containers are placed on insulating foam to prevent heat transfer and the area is free from drafts or other outside temperature interference factors. The timing of the chemical reaction starts when the components have all been added to the closed containers and the temperature is recorded at frequent intervals. A temperature reading is taken at three minutes to determine whether the composition has a fast activation characteristic, the lowest temperature is noted and the time duration that the composition remains below 45°F. is noted as well as whether the composition has a reusability feature. The results are shown in Table I as follows.

Table I

| Ex. | Temp. °F. at 3 Minutes | Lowest Temp. °F. | Time (Minutes) Temp. Below 45°F. | Reusability Feature |
| --- | --- | --- | --- | --- |
| 1 | 30 | 27 | 86 | No |
| 2 | 70 | 34 | 215 | No |
| 3 | 21 | 14 | 176 | No |
| 4 | 45 | 27 | 150 | Yes |
| 5 | 25 | 18 | 150 | Yes |

The only compositions that satisfy the desired cold pack device requirements of fast activation, long duration and reusability as previously defined are the compositions of the present invention as embodied in Examples 4 and 5. In each of the other compositions, one or more of the requirements of a desirable product are not achieved, e.g., the composition of Example 1 does not provide long duration of cold or reusability; the composition of Example 2 does not provide fast activation or reusability; and the composition of Example 3 does not provide reusability.

EXAMPLE 6

83.5 Grams of sodium acetate trihydrate and 25.5 grams of ethylene glycol are mixed and agitated for 15 seconds in a glass jar equipped as in Examples 1-5. The temperatures of each component prior to mixing and agitation and the temperature of the mixture after agitation are recorded as follows:

Temperature (°F.) of $NaC_2H_3O_2.3H_2O$ before mixing — 73

Temperature (°F.) of ethylene glycol before mixing — 73

Temperature (°F.) of mixture after agitation — 54.

This indicates that the water miscible organic liquid, e.g., ethylene glycol, enters into an endothermic reaction with the salt hydrate, e.g., sodium acetate trihydrate, thereby lowering the temperature and is, therefore, a co-reactant with the salt, e.g., ammonium nitrate, which also reacts endothermically with the salt hydrate.

In addition to the preferred embodiments described herein, other embodiments, arrangements and variations within the spirit of the invention and the scope of the appended claims will occur to those skilled in the art.

What is claimed is:

1. A method of applying cold to a part of the body comprising applying a fast activation, long duration, reusable cold pack device comprising ammonium nitrate, sodium acetate trihydrate and an aqueous solution of ethylene glycol wherein said components are separated until activation is desired but when activated by admixing, an endothermic reaction occurs resulting in a lowering of the temperature of the device.

2. A fast activation, long duration, reusable cold pack device comprising an anhydrous salt selected from the group consisting of ammonium nitrate, potassium nitrate and ammonium chloride, a salt hydrate selected from the group consisting of sodium acetate trihydrate, sodium carbonate decahydrate, sodium sulfate decahydrate, sodium thiosulfate pentahydrate and sodium phosphate dodecahydrate and a water-miscible organic liquid selected from the group consisting of alkylene glycols containing from two to four carbon atoms, wherein said anhydrous salt, salt hydrate and water-miscible organic liquid are initially separated until activation is desired but when activated by admixing, an endothermic reaction occurs resulting in a lowering of the temperature of the device.

3. The cold pack device of claim 1 wherein the anhydrous salt is ammonium nitrate.

4. The cold pack device of claim 1 wherein the salt hydrate is sodium sulfate decahydrate.

5. The cold pack device of claim 1 wherein the salt hydrate is sodium acetate trihydrate.

6. The cold pack device of claim 1 wherein the water-miscible organic liquid is ethylene glycol.

7. The cold pack device of claim 1 wherein the water miscible organic liquid is initially admixed with a suitable amount of water to form an aqueous solution.

8. A fast activation, long duration, reusable cold pack device comprising ammonium nitrate, sodium acetate trihydrate and an aqueous solution of ethylene glycol wherein said components are separated until activation is desired but when activated by admixing, an endothermic reaction occurs resulting in a lowering of the temperature of the device.

* * * * *

UNITED STATES PATENT AND TRADEMARK OFFICE
CERTIFICATE OF CORRECTION

PATENT NO. : 3,977,202
DATED : August 31, 1976
INVENTOR(S) : Forusz, Samuel L. et al It is certified that error appears in the above-identified patent and that said Letters Patent are hereby corrected as shown below:

Page 1, "Inventors" The name "Cross" should read --- Gross ---.

Claims:

Claim 1 should read Claim 8

Claim 2 should read Claim 1

Claim 3 should read Claim 2

Claim 4 should read Claim 3

Claim 5 should read Claim 4

Claim 6 should read Claim 5

Claim 7 should read Claim 6

Claim 8 should read Claim 7

Signed and Sealed this nineteenth Day of July 1977

[SEAL]

Attest:

RUTH C. MASON
Attesting Officer

C. MARSHALL DANN
Commissioner of Patents and Trademark